United States Patent [19]

Cresswell et al.

[11] 4,088,750

[45] May 9, 1978

[54] METHOD AND PREPARATION FOR INCREASING BIOAVAILABILITY OF DIGOXIN

[75] Inventors: Ronald M. Cresswell, Raleigh; Elvin A. Holstius, Greenville, both of N.C.

[73] Assignee: Burroughs Wellcome Co., Research Triangle Park, N.C.

[21] Appl. No.: 653,246

[22] Filed: Jan. 28, 1976

Related U.S. Application Data

[63] Continuation-in-part of Ser. No. 444,961, Feb. 22, 1974, abandoned, and a continuation-in-part of Ser. No. 453,000, Mar. 19, 1974, abandoned.

[51] Int. Cl.² ............... A61K 9/48; A61K 31/705
[52] U.S. Cl. ............................. 424/37; 424/182
[58] Field of Search ............................. 424/37, 182

[56] References Cited

U.S. PATENT DOCUMENTS

| | | | |
|---|---|---|---|
| 2,298,122 | 10/1942 | Hailer et al. | 424/37 |
| 2,415,312 | 2/1947 | Thompson et al. | 424/182 |
| 2,698,822 | 1/1955 | Halpern et al. | 424/182 |
| 2,765,256 | 10/1956 | Beals et al. | 424/182 |
| 2,780,355 | 2/1957 | Palermo et al. | 206/84 |
| 2,860,086 | 11/1958 | Stoll et al. | 424/182 |
| 3,139,383 | 6/1964 | Neville | 424/37 |
| 3,418,999 | 12/1968 | Davis | 424/14 |
| 3,536,074 | 10/1970 | Aufhauser | 128/222 |
| 3,784,684 | 1/1974 | Bossert et al. | 424/37 |
| 3,867,521 | 2/1975 | Miskel et al. | 424/37 |

OTHER PUBLICATIONS

HOM et al. J. PHARM. SCI. 59(6): 827-830 June 1970, "Oral Dosage Form Design and its Influence on Dissolution Rates for a Series of Drugs".
Huffman et al. J.A.M.A. 222(8): 957-960 Nov. 20, 1972, "Absorption of Orally Given Digoxin Preparations".
Lindenbaum Pharmacol. Rev. 25(2): 229-237 June 1973, "Bioavailability of Digoxin Tablets".

*Primary Examiner*—Shep K. Rose
*Attorney, Agent, or Firm*—Donald Brown

[57] ABSTRACT

Method and preparation for increasing the bioavilability of digoxin to treat cardiac insufficiency in a human, said method comprising the administration of a preparation comprising a capsule adapted to release a solution of digoxin in an amount sufficient to treat cardiac insufficiency.

9 Claims, No Drawings

METHOD AND PREPARATION FOR INCREASING BIOAVAILABILITY OF DIGOXIN

PRIOR APPLICATION

This application is a continuation-in-part of our prior application Ser. No. 444,961 filed Feb. 22, 1974 (now abandoned) and Ser. No. 453,000 filed Mar. 19, 1974, now abandoned.

BRIEF STATEMENT OF THE DISCLOSURE

The present invention is directed to the discovery of a new and improved method of increasing the bioavailability (concentration) of digoxin in the blood by administering a soft gelatin capsule containing a solution of digoxin. With the present invention substantially higher concentrations of digoxin in the blood are achieved in comparison with using tablets containing the same amount of digoxin or the same solution of digoxin as in the capsule given orally without being encapsulated.

In addition, the capsule herein unexpectedly appears to provide substantially the same amount of digoxin in comparison with digoxin given intravenously. The capsule herein also provides a higher concentration of digoxin to the patient than a standard pediatrics elixir containing digoxin (sold under the brand name LANOXIN ®.)

This invention also relates to pharmaceutical preparations containing a solution of digoxin in a capsule which will rapidly release digoxin for uptake preferably in the upper gastrointestinal tract of a human.

The glycoside digoxin, chemically named 3α-tri-(β-D-digitoxosyl)oxy-12α,14β-dihydroxy-5β-card-20(22)-enolide, has found extensive use in the treatment of human patients with cardiac insufficiency. As used herein the term cardiac insufficiency is intended to include congestive heart failure, atrial fibrillation, atrial flutter, supraventricular tachycardia and premature extrasystoles.

In the past, patients, i.e. adults, have generally been administered digoxin orally in the form of tablets containing normally 0.125 mg, 0.25 mg, and 0.5 mg of digoxin. As used herein the term patient when used is meant to be a human patient.

In cases where rapid digitalization to treat cardiac insufficiency is desired in one day or less, the patient is normally 0.5-1.5 mg of digoxin initially followed by 0.25 to 0.5 mg of digoxin every six to eight hours as required to complete digitalization. In elderly patients, and where there is less urgency, a smaller initial dose of 0.25 to 1.0 mg of digoxin may be given. In general, the average total digitalizing dose of digoxin for the patient is 2 to 3 mg. Thereafter maintenance doses of about 0.125 mg to 0.5 mg digoxin is administered daily.

Digoxin is known to be a drug in which the therapeutic blood levels are quite close to, and indeed sometimes overlap with the blood levels causing toxic symptoms such as anorexia, nausea, vomiting, and various cardiac arrhythmias, etc. Although these symptoms are not normally encountered in titrated patents having digoxin uptake or absorption within normal limits, patents which exhibit abnormal digoxin uptake may be at considerable risk.

Patients with abnormal uptake due to conditions such as greatly increased gastrointestinal mobility often require larger than normal doses of digoxin to evoke appropriate digitalization. Clearly, in such patients receiving larger than normal doses the greater the variation and the quantity of digoxin available for uptake the greater the risk that the therapeutic to toxic threshold will be crossed. All oral digoxin preparations investigated to date and known to us have been less than completely absorbed and hence have the potential for variable absorption. The present invention reduces the risk for variable uptake because it significantly reduces the incompleteness of absorption.

BRIEF STATEMENT OF THE INVENTION

The invention herein is directed to a new and improved method and preparation for increasing the bioavailablity of digoxin. In this invention, digoxin is administered to a patient in an amount which is approximately 80% of the dosage utilized in conventional tablets to achieve substantially the same blood level of digoxin in the patient. The aforementioned increased bioavailability is accomplished by the utilization of a solution of digoxin in a soluble capsule shell, e.g. soluble in the upper gastrointestinal tract. The capsule preferably comprises a soft gelatin shell which will substantially completely dissolve within the upper gastrointestinal tract in a short period of time preferably less than one-half hour and most preferably less than 15 minutes to release a solution containing an effective cardiac insufficiency treatment amount of digoxin. As used herein the upper gastrointestinal tract is defined as the stomach and the duodenum, as used herein the term solution of digoxin obviously means a pharmaceutically or medicinally acceptable solution of digoxin, as used herein the term solution obviously means a pharmaceutically or medicinally acceptable solution and as used herein the term pharmaceutically or medicinally acceptable obviously means acceptable to the gastrointestinal tract of the patient, and as used herein the term solution is intended to include a solution in which at least a portion of the digoxin in the capsule is in solution.

The capsule shell when preferably made of gelatin may include plasticizers such as glycerin or sorbitol, water, preservatives, coloring agents(s), and opacifying agent(s). Reference may be had to Remington's Practice of Pharmacy, Martin and Cook, Twelfth Edition, pages 467 under the heading Elastic Capsules to page 469 for a description of gelatin capsules rapidly dissolvable in the gastrointestinal tract and the manufacture of such capsules, all of which are incorporated by reference herein. Reference may also be had to U.S. Pat. No. 2,899,361 as well as 2,928,128 for a description of soft gelatin capsules and their manufacture, both of said patents being incorporated herein by reference hereto. In addition reference may also be had to the book "The Theory and Practice of Industrial Pharmacy" by Lackman, Lieberman and Kanig (1970) pages 359–389 published by Lea and Febiger, Philadelphia, Pennsylvania for a discussion of soft gelatin capsule technology said text pages 359–389 being incorporated herein by reference hereto. The digoxin is placed in solution prior to being encapsulated. A suitable solution may be prepared by conventionally mixing digoxin with solvents such as ethanol, propylene glycol, isopropanol, and polyethylene glycols such as polyethylene glycol 400 or a combination thereof. In addition, other solvents which may be added to the aforementioned solvents as a cosolvent include glycerin and polyvinylpyrrolidine, among others.

Polyethylene glycols having average molecular weights between 190 and 6000 and containing 2 to 136 ethylene glycol monomer units (CH$_2$CH$_2$O) advantageously be used as a cosolvent and polyethylene glycols having average molecular weights between 190 to 1000 and containing about 2 to 25 ethylene glycol monomer units as above may advantageously be used as a solvent or cosolvent.

Other solvents or cosolvents which would also be suitable include 1,2-propylene glycol, hexamethylene glycol, 1,3-butylene glycol, dimethylsulfoxide, polyethylene glycol ethers of tetrahydrofurfuryl alcohol and di(1,2-propylene glycol). In addition up to 5% water may be used as a co-solvent.

As used herein the term solvent obviously means a solvent which is pharmaceutically or medicinally acceptable to the gastrointestinal tract and which will dissolve digoxin to form a solution and is not substantially destructive of the capsule shell.

The capsules of this invention are preferably enlongated such as ellipsoidal, oval or cylindrical with rounded ends. In its most preferred form the capsules contain a solution containing either 0.2 mg digoxin, 0.1 mg digoxin or 0.05 mg digoxin. A range of about 0.2 mg to about 0.05 mg of digoxin may also preferably be used, with each capsule containing less digoxin being preferably smaller in physical size. Preferably, each capsule contains digoxin in solution at a concentration of 0.25 to 0.6 mg/ml with a concentration of 0.35 to 0.55 mg/ml being more preferred and a concentration of 0.4 to 0.5 mg/ml being most preferred. As used herein, concentration means mg of digoxin/ml of solution. The soft gelatin capsules are chosen from those available from various manufacturers to hold the volume of the following examples to provide the concentration set forth therein.

As used herein the term an effective cardiac insufficiency treatment amount of digoxin means one or more capsules of the type disclosed herein, with each capsule preferably containing a solution of 0.05 mg digoxin, 0.1 mg digoxin, or 0.2 mg digoxin. For initial digitalizing of patients to treat cardiac insufficiency a dose of about 0.4 to 1.2 mg digoxin followed by about ¼ to ⅓ of the initial digoxin dose every 6 to 8 hours for 24 hours to complete digitilization may be used. Thereafter maintenance doses of 0.1 to 0.4 mg digoxin per day may be administered depending upon the patient.

EXAMPLE I

The following comparative example illustrates the unexpected properties of a capsule containing digoxin in solution in comparison with tablets containing digoxin in dry form at the same dose or in a greater dose than in the capsule.*

* All capsules and tablets used in this example were tested in Quality Control to insure content uniformity.

The procedure used for obtaining the results is as follows:

Eight normal subjects (human) were given each of the four following digoxin preparations with rest periods in between to permit digoxin clearance.

(A) 0.2 mg digoxin in solution in soft gelatin capsule shell - dissolution rate (dr) 100% at 1 hour.

(B) 0.2 mg digoxin in tablet - dr 97% at 1 hour.

(C) 0.25 mg digoxin in tablet - dr 97% at 1 hour.

(D) 0.25 mg digoxin in tablet (standard Lanoxin ® brand Digoxin) - dr 78% at 1 hour.

Dosage was 2 tablets or capsules q8h x4; then 1 tablet or capsule bid (twice a day) days 3-9. Serum digoxin levels after the first dose and in the steady state (SS) (days 8-10), and 24-hour urine digoxin excretion (u.d.e.) on day 1 were measured by radioimmunoassay. Results (mean and SE's):

|   | Serum peak ng/ml | area under curve, 0-6 hr. Units | 24 hr. u.d.e, ug | SS serum ng/ml |
|---|---|---|---|---|
| A | 3.34±.53 | 451±30 | 273±21 | 1.08±.06 |
| B | 2.08±.21 | 311±16 | 206±12 | 0.91±.07 |
| C | 2.68±.30 | 448±26 | 248±13 | 1.02±.06 |
| D | 2.12±.18 | 376±14 | 260±26 | 1.17±.12 |

A was better absorbed than B, as indicated by 1 hr. (p<.05) serum levels, 24 hr. urine levels (p<.01), areas under curve (p<.001), and SS levels (p<.02). Despite smaller digoxin dosage, absorption of A was similar to C and D. There were also no significant differences between C and D. B-to-C and B-to-D differences were significant, consistent with different digoxin content. Coefficient of variation of SS values did not differ significantly among the 4 formulations. ECG changes (8 hr. monitoring) were similar with all 4. We conclude that (1) digoxin tablets of 97% dr are no better absorbed by normals that currently available tablets, and (2) a switch from tablet to solution filled capsules would require a reduction in digoxin dosage.

The soft gelatin capsule (A) contained about 0.2 mg. digoxin, a fill volume of 6.65 minims, a fill weight of 448 mg. The digoxin was dissolved in solvent comprising ethanol (absolute), water, propylene glycol, and polyethylene glycol 400. With the above fill weight the concentration would be calculated to be about 0.45 mg/ml by dividing the weight of digoxin by fill volume in ml assuming the solution has a desnity of 1.0 gr/ml. The percentage amounts of the various ingredients of the solvent are set forth in Example II.

EXAMPLE II

A suitable mixture of the solvents may obviously vary depending upon the desired concentration and composition of the solvent system.

By way of example, a suitable solvent system for digoxin at 0.2 mg may include the following ingredients and their amounts by weight:

Polyethylene glycol 400 - 90%
Ethanol(absolute) - 6%
Propylene glycol - 3%
Water - 1%

A solution of digoxin in the aforementioned solvent mixture was packaged in a conventional soft gelatin capsule shell using conventional soft gelatin capsule packaging machinery to provide soft gelatin capsules, each containing 0.2 mg of digoxin. The ingredients are conventionally stirred together and may be heated if desired to speed dissolution of the digoxin.

A solution having a concentration of 0.35 mg. of digoxin/ml, as set forth on page 4 and containing 0.2 mg of digoxin would require about 0.57 ml of solvent. This is conventionally determined by dividing the weight of the digoxin by the desired concentration of the solution assuming the weight of digoxin is negligible. For Example 1, the amount of solvents of Example II used would weigh about 447.8 mg and may be determined by subtracting the weight of digoxin from the fill weight. The concentration would be calculated as shown in EXAMPLE I.

EXAMPLE III

A soft gelatin capsule is filled with a solution containing 0.1 mg digoxin in 100% polyethylene glycol 400 by weight. To prepare a 0.25 mg/ml concentrated solution as set forth on page 4 with 0.1 mg of digoxin, the amount of polyethylene glycol 400 is calculated to be about 1.6 ml.

EXAMPLE IV

A soft gelatin capsule is filled with a solution containing 0.05 mg of digoxin in 90% polyethylene glycol 400 by weight and 10% glycerin by weight at a concentration of 0.5 mg./ml.

EXAMPLE V

A soft gelatin capsule is filled with a solution containing 0.05 mg. of digoxin and propylene glycol 100% at a concentration of 0.4 mg./ml.

EXAMPLE VI

A soft gelatin capsule is filled with a solution containing 0.2 mg. of digoxin and propylene glycol 100% at a concentration of 0.5 mg./ml.

EXAMPLE VII

A soft gelatin capsule is filled with a solution containing 0.1 mg. of digoxin, ethanol (50%) and propylene glycol (50%) at a concentration of 0.45 mg./ml.

EXAMPLE VIII

A soft gelatin capsule is filled with a solution containing 0.2 mg. of digoxin, ethanol 5%, glycerin 5%, and propylene glycol 90% at a concentration of 0.50 mg./ml.

EXAMPLE IX

A soft gelatin capsule is filled with a solution containing 0.1 mg. of digoxin, ethanol 10%, propylene glycol 89%, water 1% at a concentration of 0.43 mg./ml.

EXAMPLE X

A soft gelatin capsule is filled with a solution containing 0.1 mg. of digoxin, water 1%, propylene glycol 9% at a concentration of 0.35 mg./ml.

EXAMPLE XI

Single 0.4 mg digoxin doses dissolved in a mixture of polyethylene glycol and propylene glycol prepared as a liquid concentrate in a soft gelatin capsule were compared with the same solution above given in liquid form as well with a standard pediatric digoxin elixir in a crossover study in 10 volunteers. The mean areas under the serum concentration time curves (AUC) after the capsules (408 ± 48 U) was greater than after administration of the solution of digoxin in the capsule (i.e., absent the capsule) (308 ± 24 U) P>0.05 by paired testing) or after the pediatric elixir (309 ± 28 U; p>0.05). The two liquid preparations did not differ significantly from each other. The mean time required to reach peak serum levels was similar with the three preparations (51 ± 8; 50 ± 10; and 42 ± 5 min. respectively. The mean 24 hour urinary digoxin excretion after the capsules (105 ± 6 mg) was greater than the solution in the capsule per se (90 + 2 mg, p>0.05) or after the elixir (92 ± 5 mg. p> 0.02). See Clinical Pharmacology and Therapeutics Vol. 18, No. 6, pages 761-768.

We claim:

1. In the method of increasing the bioavailability of digoxin in a human suffering from cardiac insufficiency which comprises administering to the upper gastrointestinal tract of said human a capsule comprising a soft gelatin capsule shell containing a solution comprising digoxin in a solvent system, the improvement wherein the digoxin is in solution at a concentration of at least 0.25 mg digoxin/ml solution, said capsule containing the solution of the solvent system comprising the following ingredients in about the % amount set forth by weight:

polyethylene glycol 400 (90%)
absolute ethanol — (6%)
propylene glycol — (3%)
water — (1%) and 0.2 mg digoxin said solvent system being pharmaceutically acceptable to the gastrointestinal tract and able to dissolve digoxin to form a solution and is not substantially destructive of the capsule shell, the solution of said digoxin and solvent system being encapsulated in said shell and said capsule shell capable of being dissolved in the upper gastrointestinal tract of said human, said capsule with said solution providing a bioavailability of digoxin substantially equal to 0.25 mg digoxin administered in tablet form in the same manner as the capsule.

2. A method according to claim 1 wherein the capsule shell has a dissolution rate of substantially 100% at 1 hour.

3. The method of claim 1 in which the digoxin is in solution at a concentration of 0.25 to 0.6 mg digoxin/ml solution.

4. The method of claim 2 in which the digoxin is in solution at a concentration of 0.25 to 0.6 mg digoxin/ml solution.

5. A pharmaceutical capsule comprising a soft gelatin capsule shell containing a solution of 0.1 mg. or 0.2 mg. digoxin in said capsule shell, said capsule shell capable of dissolving in the upper gastrointestinal tract, said solution containing a solvent system which is pharmaceutically acceptable to the gastrointestinal tract and which will dissolve digoxin to form a solution and is not substantially destructive of the capsule shell, said capsule providing the same digoxin bioavailability as a comparable tablet while containing only about 80% of the amount of digoxin as in the comparable tablet, said digoxin present at a concentration of at least 0.25 mg digoxin/ml solution and said capsule containing the solvent system comprising the following ingredients in about the % amount set forth by weight:

polyethylene glycol 400 (90%)
absolute ethanol — ( 6%)
propylene glycol — ( 3%) and
water — ( 1%).

6. The capsule according to claim 5 wherein the dissolution rate of the capsule shell is substantially 100% at 1 hour in the upper gastrointestinal tract.

7. The capsule according to claim 5 wherein the capsule shell at least partially dissolves in the stomach of a human.

8. The capsule of claim 5 in which the concentration is 0.25 to 0.6 mg. digoxin/ml solution.

9. The capsule of claim 7 in which the concentration of digoxin is 0.25 to 0.6 mg. digoxin/ml solution.

* * * * *